United States Patent [19]

Wu et al.

[11] Patent Number: 5,684,239
[45] Date of Patent: Nov. 4, 1997

[54] MONOCOT HAVING DICOT WOUND-INDUCIBLE PROMOTER

[75] Inventors: Ray Wu; David McElroy; Deping Xu, all of Ithaca, N.Y.

[73] Assignee: Cornell Research Foundation, Inc., Ithaca, N.Y.

[21] Appl. No.: 303,446

[22] Filed: Sep. 9, 1994

Related U.S. Application Data

[63] Continuation of Ser. No. 770,048, Oct. 2, 1991, abandoned, which is a continuation-in-part of Ser. No. 762,680, Sep. 18, 1991, abandoned, which is a continuation of Ser. No. 461,490, Jan. 5, 1990, abandoned.

[51] Int. Cl.$^6$ .............................. A01H 4/00; C12N 15/82; C12N 15/11
[52] U.S. Cl. .................................. 800/205; 800/DIG. 52; 800/DIG. 57; 435/320.1; 536/24.1
[58] Field of Search .......................... 435/320.1, 172.3; 800/205, DIG. 52, DIG. 57; 536/24.1

[56] References Cited

FOREIGN PATENT DOCUMENTS

WO 91/09948  7/1991  WIPO.

OTHER PUBLICATIONS

Wang, Y., et al., Molecular and Cellular Biology 12(8):3399–3406 (1992).
Reece, K.S., et al., Plant Molecular Biology 14:621–624 (1990).
Gonzalez-y-Merchand, J.A., and Cox, R.A., J Mol Biol 202:161–168 (1988).
Brinster, R.L., et al., Proc Natl Acad Sci USA 85:836–840 (1988).
McElroy, D., et al., Plant Molecular Biology 15:257–268 (1990).
Vandekerckhove, J. and Weber, K., Nature 276:720–721 (1978).
McElroy, D. et al., Plant Molecular Biology 14:163–171 (1990).
McElroy, D. et al., The Plant Cell 2:163–171 (1990).
McElroy, D. et al., Mol Gen Genet 231:150–160 (1991).
Nagao, R.T. et al., DNA 2(1):1–9 (1981).
Ng, SY et al., Nucleic Acids Research 17(2):601–615 (1989).
Shah, D.M. et al., Journal of Molecular and Applied Genetics 2:111–126 (1983).
Staiger, C.J. et al., Protoplasma 141:1–12 (1987).
Zhang, W. et al., The Plant Cell 3:1155–1165 (1991).
McElroy, D. et al., J Cellular Biochem, Supplement 15A:75, abstract No. A 335 (1991).
Sanchez-Serrano, J.J., et al., The EMBO Journal 6(2):303–306 (1987).
Xu, D., et al., Plant Molecular Biology 22:573–588 (1993).
Palm, C.J., et al., Proc Natl Acad Sci USA 87:603–607 (1990).
Ryan, C.A., BioEssays 10(1):20–24 (1989).
Farmer, E.E. and Ryan, C.A., Proc Natl Acad Sci USA 87:7713–7716 (1990).
Thornburg, R.W., et al., Proc Natl Acad Sci USA 84:744–748 (1987).
Sanchez-Serrano, J.J., et al., Proc Natl Acad Sci USA 87:7205–7209 (1990).
Keil, M., et al., The EMBO Journal 8(5):1323–1330 (1989).
Ryan, C.A., Annu Rev Phytopathol 28:425–449 (1990).
Ryan, C.A. and An, G., Plant, Cell and Environment 11:345–349 (1988).
Thornburg, R.W., et al., Plant Physiol 92:500–505 (1990).
Xu, D., et al., J Cellular Biochem, Supplement 16F:223, abstract No. Y235 (1992).
Keil, et al., Nucleic Acids Res 14(14):5641–5650 (1986).
Schaffner and Sheen, Plant Cell 3(9):997–1012 (1991).
Peterhans, et al., Mol Gen Genet 222(2–3):361–368 (1990).
Christensen, et al., Plant Mol Biol 18(4):675–689 (1992).
U.S. application No. 07/762,680, Wu et al., filed Sep. 18, 1991.
U.S. application No. 08/144,602, McElroy et al., filed Oct. 27, 1993.
Klopfenstein, et al (Sep. 1991) Canadian Journal of Forest Research 11 (9):1321–1328.
Keil, et al (Jan. 1990) The Plant Cell 2:61–70.
Callis, et al (1987) Genes and Development 1:1183–1200.
Oard, et al (1989) Plant Cell Reports 8:156–160.
Frederickson, et al (1989) Nucleic Acids Research 17(1):253–270.
Nairn, et al (1988) Gene 65:247–257.

*Primary Examiner*—Che S. Chereskin
*Attorney, Agent, or Firm*—Nixon, Hargrave, Devans & Doyle

[57] ABSTRACT

The present invention describes the activity of a dicot wound inducible promoter in a monocot plant, the use of a monocot intron to enhance the activity of a dicot promoter in a transgenic monocot, and genetic constructs to introduce an exogenous genetic trait into a monocot plant using a wound inducible dicot promoter system.

4 Claims, 6 Drawing Sheets

FIG. 1C

FIG. 1D

KEY: (FIGS 2B-2J)

☒ PinII 5' AND 3' ENDS    ☐ Act1-5' EXON
☐ Act1-5' INTRON    ▨ Act1-5' END

TRANSLATIONAL FUSION VECTOR READING FRAMES pDX202
pDX402 pDX216
pDX416 pDX227
pDX427

```
                          AccI    NcoI                              EcoRV
                    ag/GTAGACC ATG GCT GAC GCC GAG GAT
                          AccI    NcoI              SstII    EcoRV
                    ag/GTAGACC ATG GCC GCG GGA T

BamHI SmaI
                    ag/GTAGAAG ATG GCT GAC GCC GAG GAT GGG GGA TCC CC
```

|—1 kbp—|

FIG.2A

FIG. 2B pDX227

KpnI, ApaI, XhoI, SalI, HincII, AccI, ClaI, HindIII, EcoRV, EcoRI, PstI  XbaI, BamHI BamHI BamHI, SmaI, BamHI, SpeI, XbaI, NotI, EagI, SstII, SstI

FIG. 2C pDX202

SstI, SstII, EagI, NotI, SpeI, BamHI, SmaI, PstI  XbaI, BamHI BamHI

AccI, NcoI, EcoRV, HindIII, ClaI, SalI, HincII, AccI, XhoI, ApaI, KpnI

FIG. 2D pDX216

SstI, AccI, SalI, PstI  XbaI, BamHI BamHI

AccI, NcoI, SstII, EcoRV, SpeI, XbaI, EagI, SphI, AatII, ApaI

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
GTAGACC ATG GCT GAC GCC GAG GAT                                    25
```

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

```
GTAGACC ATG GCC GCG GGA T                                          20
```

( 2 ) INFORMATION FOR SEQ ID NO:3:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:3:

GTAGAAG ATG GCT GAC GCC GAG GAT GGG GGA TCC CC     36

MONOCOT HAVING DICOT WOUND-INDUCIBLE PROMOTER

This application is a continuation of U.S. Ser. No. 07/770,048, filed Oct. 2, 1991, now abandoned, which was a continuation-in-part of U.S. Ser. No. 07/762,680, filed Sep. 18, 1991, now abandoned, which was a continuation of U.S. Ser. No. 07/461,490, filed Jan. 5, 1990, now abandoned.

Extensive research into the effects of proteinase inhibitors on insects first began about 1955 when it was found that a protein fraction from soybeans inhibited the growth, as well as in vitro proteolytic enzyme activity of the meal worm [see Food Chem. 2:410 (1954)]. Eventually this line of research led to the discovery of wound inducibility of two proteinase inhibitor proteins, referred to as potato proteinase inhibitor I (PINI) and potato proteinase inhibitor II (PINII) proteins, in plant leaves in response to insect attack [see Science 175:776 (1972)]. One of these inhibitors, potato proteinase inhibitor II, was determined to be an inhibitor of both trypsin and chymotrypsin proteinases (proteinases are also known as proteases). Subsequent research showed these two proteinase inhibitors to be small proteins which were not present in unwounded leaves of young plants, but which could be induced to accumulate in leaves within 4 to 6 hours following wounding. Furthermore, the inhibitors were found to accumulate in both wounded and unwounded leaves of wounded plants, thus indicating that a systemic signal was generated at the wound sites and travelled rapidly throughout the plant.

Insect damage to plant leaves can cause a dramatic increase in the levels of protease inhibitor in various plant parts, apparently as a defensive response of the plants. Using tomato plants, Broadway [see Entomol. Exp. Appl. 41:33 (1986)] demonstrated that leaves from plants which had been induced by wounding could accumulate over 200 μg protein per gram of leaf tissue of potato protease inhibitors I and II. This amount was sufficient to severely reduce the growth rate of the beet armyworm.

In direct tests used to determine the roles of proteinase inhibitors to defend against insect damage [see Nature 330:160 (1987)], transformed tobacco plants expressing a gene that encodes a foreign cowpea trypsin inhibitor (an antinutrient agent against a wide range of insects including larvae of Heliothis, Spodoptera, Diabrotica, and Tribolium—all agronomically important insect pests) and producing about 1% of leaf proteins as the inhibitor were more resistant to feeding by larvae of *Heliothis virescens* than untransformed control plants or transformed plants that did not express the gene. Recent reports have also indicated that leaves of tobacco plants transformed with genes encoding the proteinase inhibitor II proteins produced proteinase inhibitor II at levels of 50 μg/g tissue (or more), and when supplied to larvae of *Manduca sexta* as their only food source, caused inhibition of larval growth and eventual death.

The premise upon which studies involving wound inducible expression of inhibitor proteins has been based is that the plants produce such inhibitors as a defensive reaction to an insect attack upon plant integrity. Support for this premise is that the inhibitors appear only after a wounding; prior to an insect eating away or otherwise disrupting the plant structure, the inhibitor is not present in the plant tissue. Wound inducible genes that encode inhibitor proteins have been extensively studied both in plants genetically inherently capable of expression upon wounding, and in plants not inherently capable of inhibitor gene expression upon wounding but which have been transformed with the genetic information required to bring about expression of the genes that encode the inhibitors upon wounding. However, prior to the making of the present invention, there has been nothing reported in the scientific literature indicating the successful activation of a dicot wound inducible promoter in a monocot plant; in addition, the present invention is the first report of the successful use of a monocot intron to enhance the activity of a dicot wound inducible promoter in a transgenic monocot.

As used in accordance with the present invention, "monocot" refers to plants belonging to the subclass Monocotyledoneae, and "dicot" refers to plants belonging to the subclass Dicotyledoneae. Among the commercially important monocots which may be transformed with the wound inducible promoter according to the present invention are rice, wheat, barley, oats, sorghum, and maize. Within the following description of the present invention, the use of rice is meant to be descriptive of the monocot subclass of plants; the present invention should not be considered to be limited to only rice.

Also as used in accordance with the present invention, "foreign gene of interest" refers to a gene encoding for the expression of proteins having natural insecticidal or antiviral activities in transgenic monocot plants, and also encompasses a plurality of genes having mixed insecticidal and antiviral activities. The insecticidal protein genes include the potato protease inhibitor II and inhibitor I genes, cowpea trypsin inhibitor (CPTi) gene, and various *Bacillus thuringiensis* endotoxin genes. The antiviral genes include genes which encode proteins which control insect-transmitted viral diseases, including but not limited to tungro virus, dwarf virus, black-streaked dwarf virus, and hoja blanca virus infection, and are based upon viral coat protein, antisense RNA, or an enzymatic requirement for viral infection, replication, or release. The foreign gene of interest may be substituted in place of the GUS coding regions, or inserted at an appropriate site within the expression vectors, depicted in the accompanying drawings.

The loss of rice yield due to insect pests is estimated to be at least several billion dollars a year [see Heinrichs, E. A., F. G. Medrano, and H. R. Rapusas, Genetic Evaluation For Insect Resistance in Rice, pg 1, IRRI, Los Banos, Philippines (1985)]. The important insect pests of rice include yellow stemborer, striped stemborer, leaffolder, gall midge, brown planthopper, whitebacked planthopper, and green leafhopper. It is also known that several devastating viral diseases are transmitted by insects as, for example, tungro virus, dwarf virus, black-streaked dwarf virus, and hoja blanca virus, all of which are known to be transmitted by rice planthoppers or leafhoppers.

Most insects have trypsin or chymotrypsin-like proteases in their digestive systems. Thus, introducing the appropriate protease inhibitor genes into rice plants should make the plants insect tolerant—the premise upon which the research that went into the making of the present invention was conducted. Reducing insect predation will also minimize the transmission and spreading of certain insect-borne viral diseases. It is obvious that the production of insect-tolerant plants by introducing genes encoding protease inhibitors or other natural insecticides, such as *Bacillus thuringiensis* (B.t.) endotoxins [see Critical Rev. Biotechnol. 6:163 (1987)] into plants is much preferred over the spraying of plants with synthetic chemical insecticides.

The different B.t. toxins have been used to kill insects by spraying plants with the crude B.t. toxins. The B.t. toxins are specific for lepidopteran insects and exhibit no harmful activity against humans, other vertebrates, and beneficial insects. Thus, the genes of these insect-killing proteins are attractive candidates for genetic engineering of crop plants for protection against lepidopteran pests.

Proteinase inhibitors provide natural defenses against insect attack by acting on the primary digestive enzymes in certain insects. Proteinase inhibitors present in dicot plants have been found to be active against a wide range of insects [see BioEssays 10:20 (1989)]. The potato gene family encoding the serine-type proteinase inhibitor II (PINII) is by far one of the best analyzed systems of systemic gene activation in response to insect attack [see EMBO 8:1323 (1989); and Proc. Natl. Acad. Sci. USA 87:7205 (1990)]. PinII is constitutively expressed in the tubers and young floral buds of normal greenhouse grown potato plants. However, when potato leaves are mechanically wounded to mimic the attack of a chewing insect, PinII gene expression is induced not only in the wounded leaves, but also in the upper and lower leaves and upper part of the stem. When the promoter of a potato PinII fused to a β-glucuronidase (GUS) reporter gene was introduced into potato and tobacco plants, the PinII-Gus gene activity was found to follow the same pattern of expression as the endogenous PinII gene in potato. When expressed at relatively high levels, the production of proteinase inhibitors has resulted in insect-tolerant transgenic tobacco plants [see Nature 330:160 (1987); Out. Ag. 18(1) (1989); and Proc. Natl. Acad. Sci. USA 86:9871 (1989)]. Although the techniques necessary for introducing the constructed gene into monocots follow those for introducing the gene into potato, tobacco or other dicot species, prior to the making of the present invention, a foreign gene fusion containing a dicot wound inducible promoter, and a monocot intron, has not been successfully expressed in a monocot.

Since the potato protease inhibitor II inhibits both trypsin and chymotrypsin-like proteases, it was selected as the first choice for introducing PinII-containing constructs according to the present invention into a monocot. Rice is a major crop in the world and the techniques have been developed and used for many years in transforming and regenerating this monocot. In addition, rice can be easily transformed and be grown under greenhouse conditions. Thus, rice was selected for the initial research leading to the present invention.

Purified B.t. endotoxins have had a long history of safe use as insecticides because they are non-toxic to non-target organisms and are rapidly biodegraded in the environment [see Tibtech. 9:197 (1991)]. However, their use has been limited by the low stability of the B.t. protein in the field and the relatively high cost of B.t. toxin production and application. In general, single B.t. endotoxins display a narrow range of target insects. Several genes encoding different B.t. toxins have been cloned and the expression of individual B.t. toxin genes has been widely studied in transgenic dicot plants [see Plant Physiol. 85:1103 (1989)].

The present invention was approached with the goal that if the B.t. endotoxin could be expressed in transgenic rice plants, this should preclude the need for repeated spraying of field crops with expensive insecticides, and kill the target insects before significant damage could occur. However, the major potential disadvantage to expressing B.t. endotoxins in transgenic plants, whether monocots or dicots, is that insect resistance might develop over a period of time.

When using transgenic plants expressing one or a variety of natural insecticides, the aim should be to keep selection pressure for the insects as low as possible in order to minimize the development of resistant pests. Restricting the expression of such natural insecticides to those plant tissues which are most susceptible to pest damage should decrease selection pressure while still providing adequate protection. Constitutive and high-level expression of a foreign gene in plants may have undesirable effects on the growth and development of the plants. Thus, an aspect of the research leading to the present invention was to produce transgenic plants that express foreign genes of interest, and mainly natural insecticides only in direct response to specific insect associated damage. This aspect led to the present invention of utilizing a dicot wound-inducible promoter for bringing about production of a naturally occurring insecticidal protein in a monocot plant.

Figure 1A:
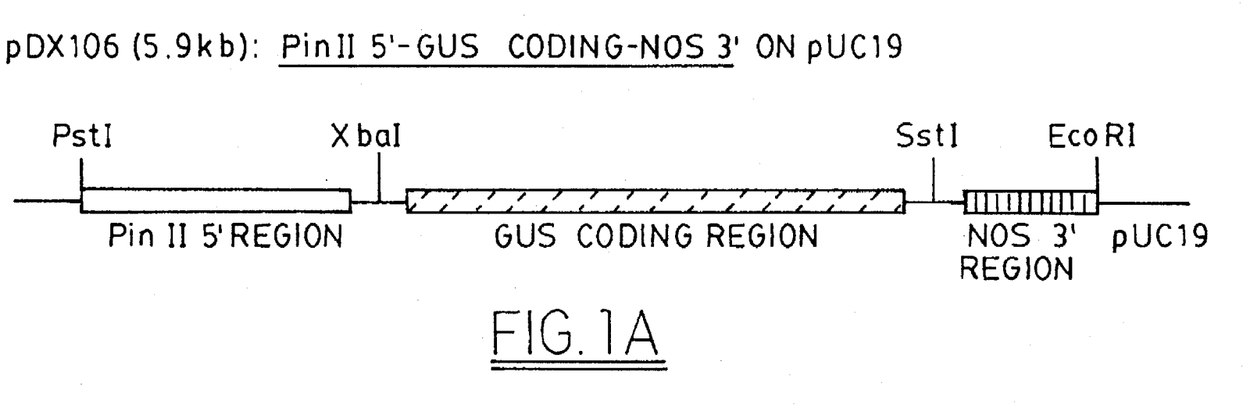
Figure 1B:
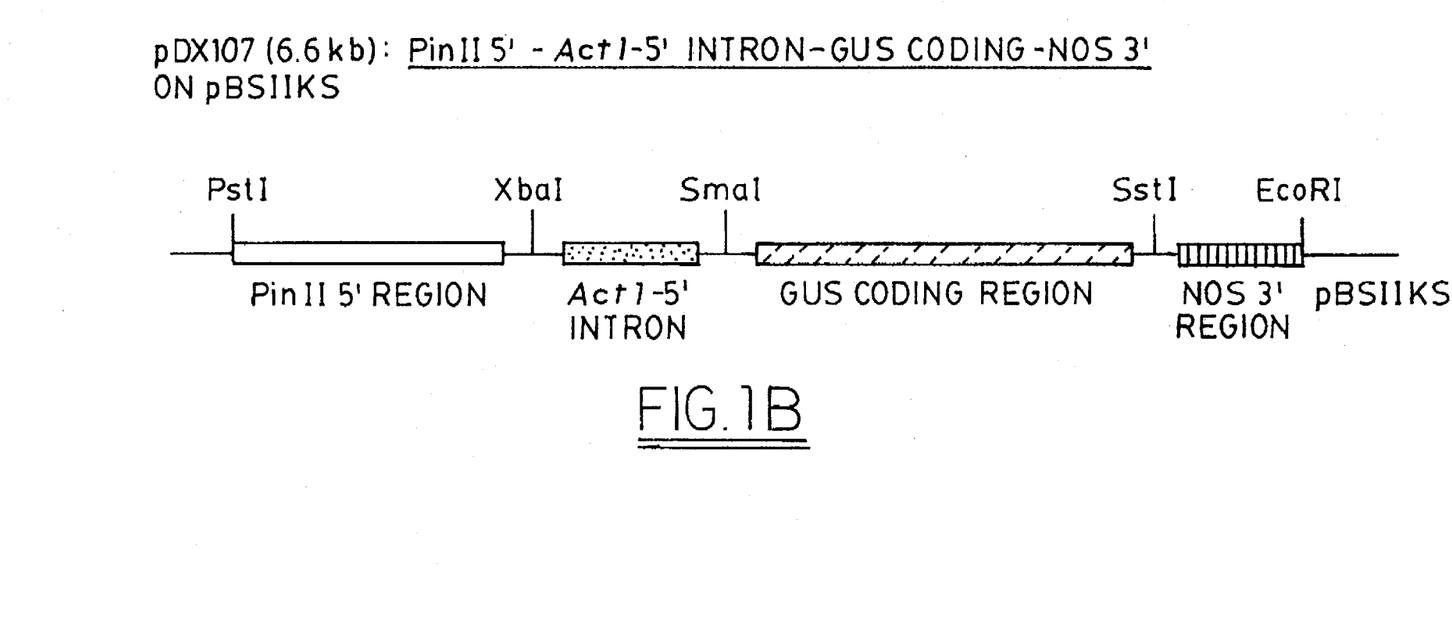
Figure 1C:
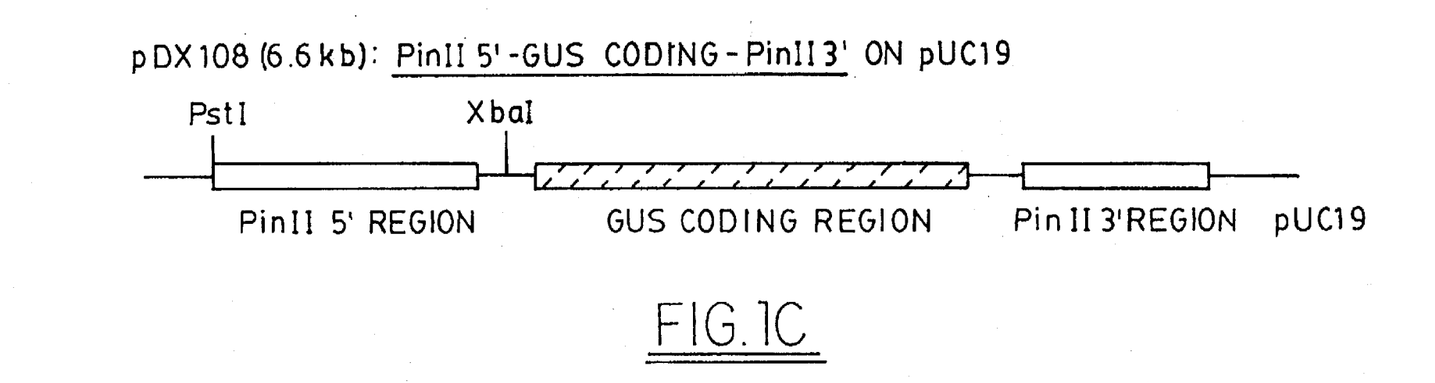
Figure 1D:
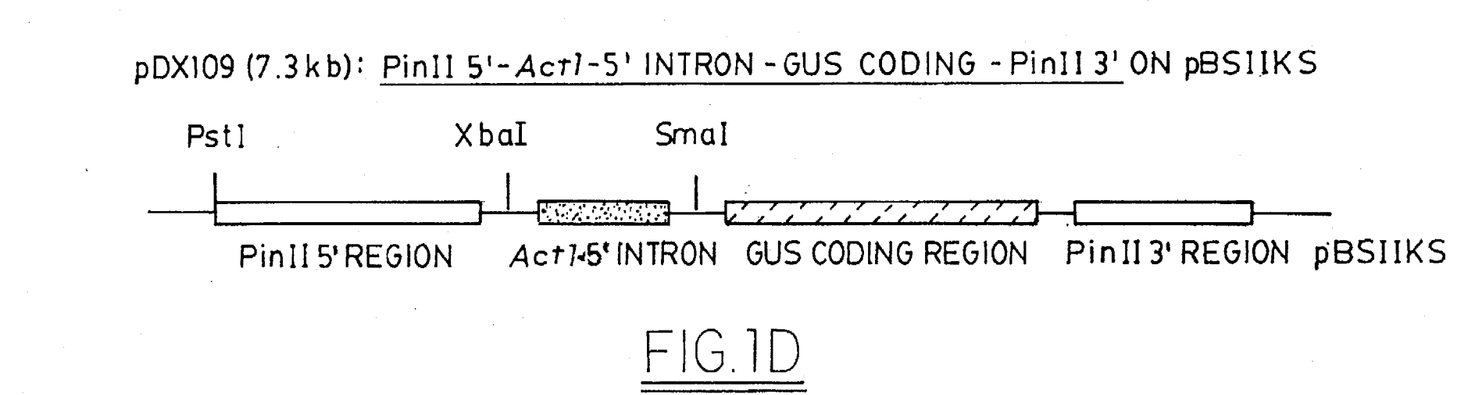
Figure 2A:
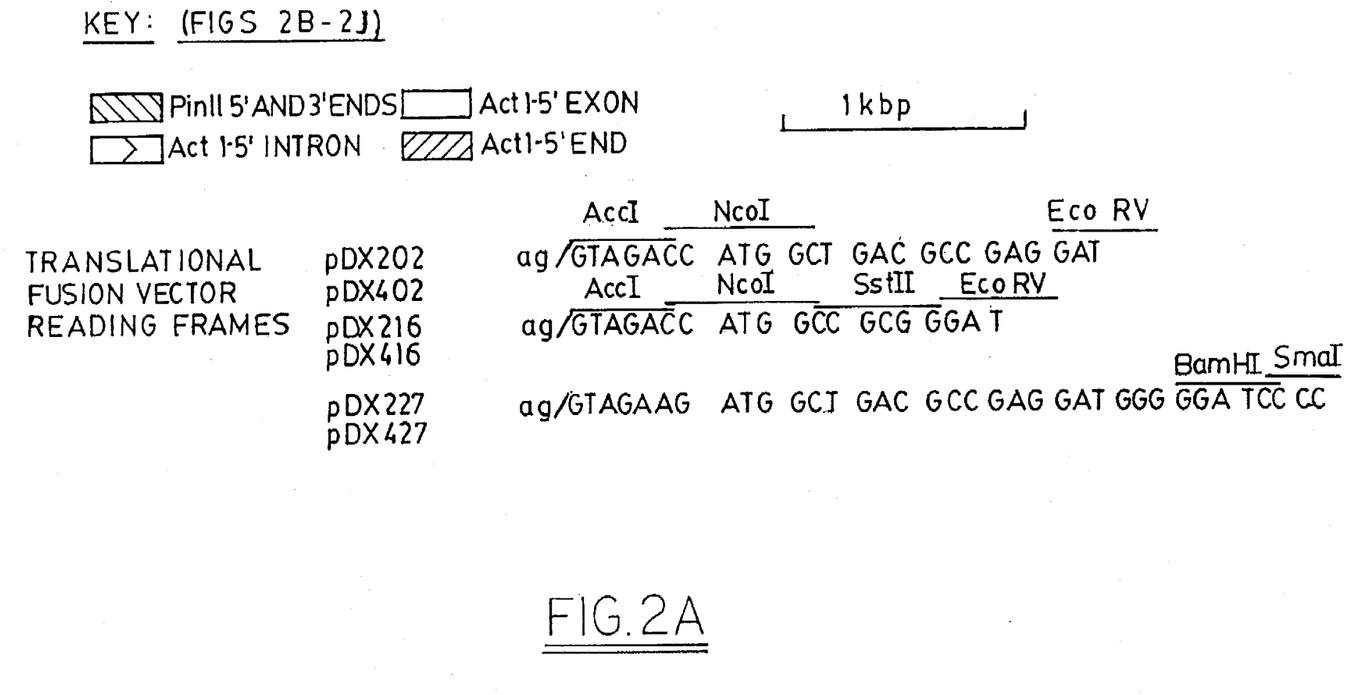
Figure 2B:
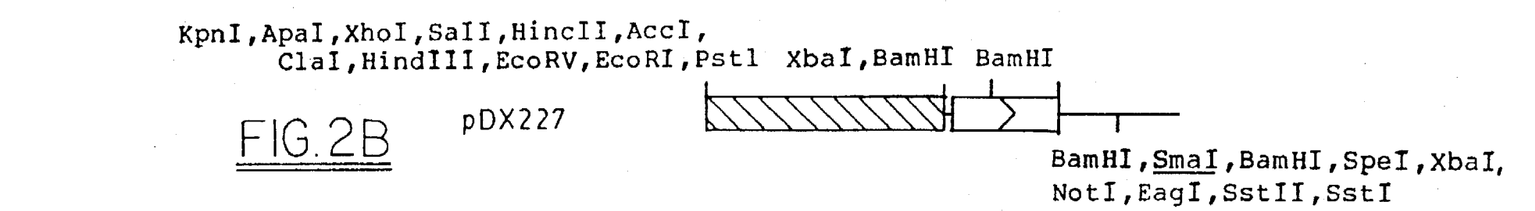
Figure 2C:
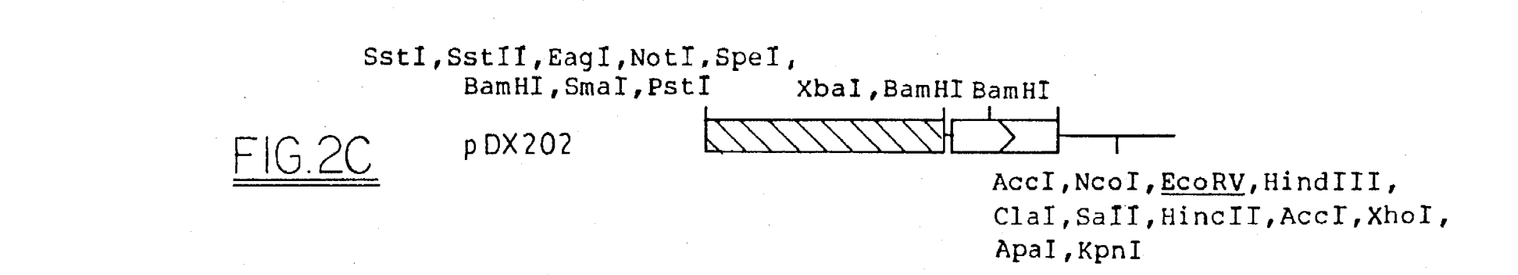
Figure 2D:
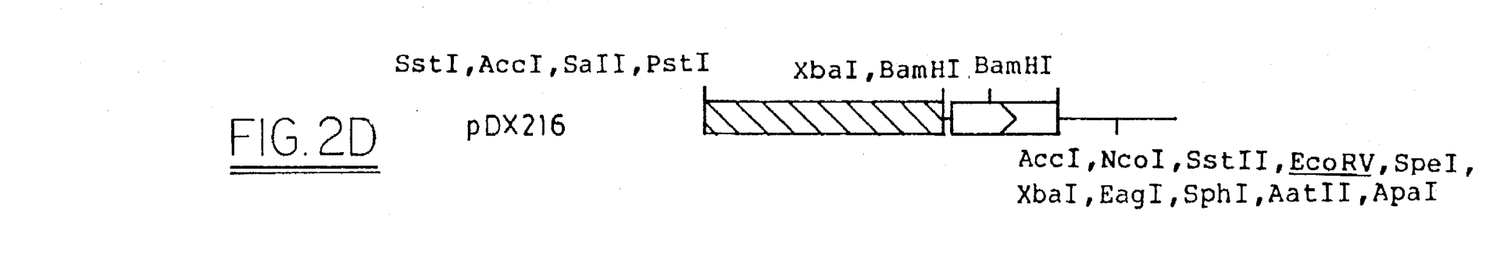
Figure 2E:
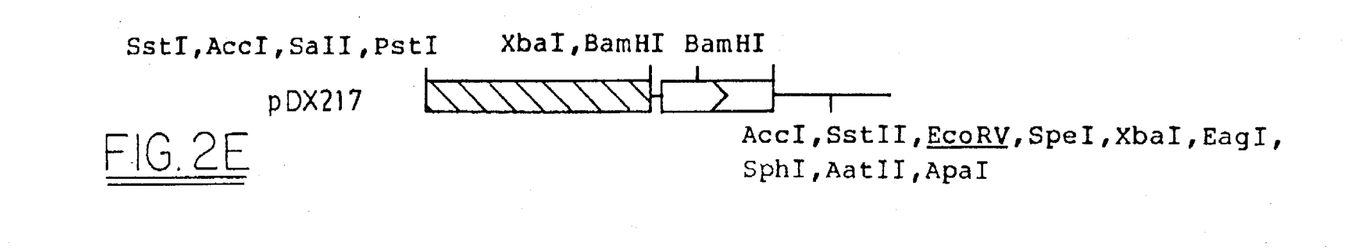
Figure 2F:
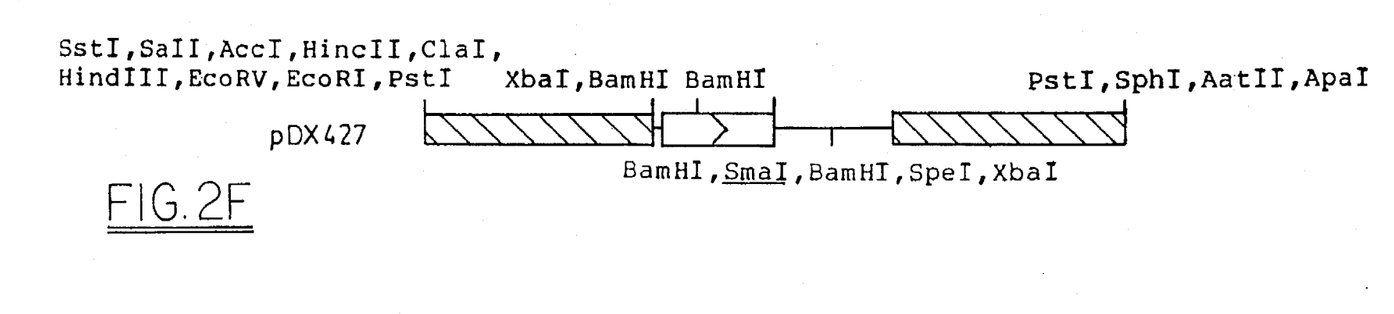
Figure 2G:
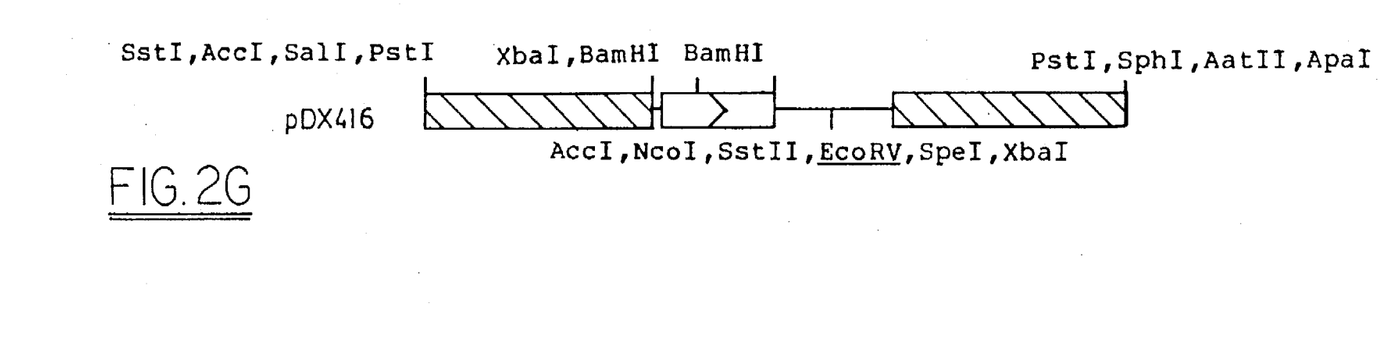
Figure 2H:
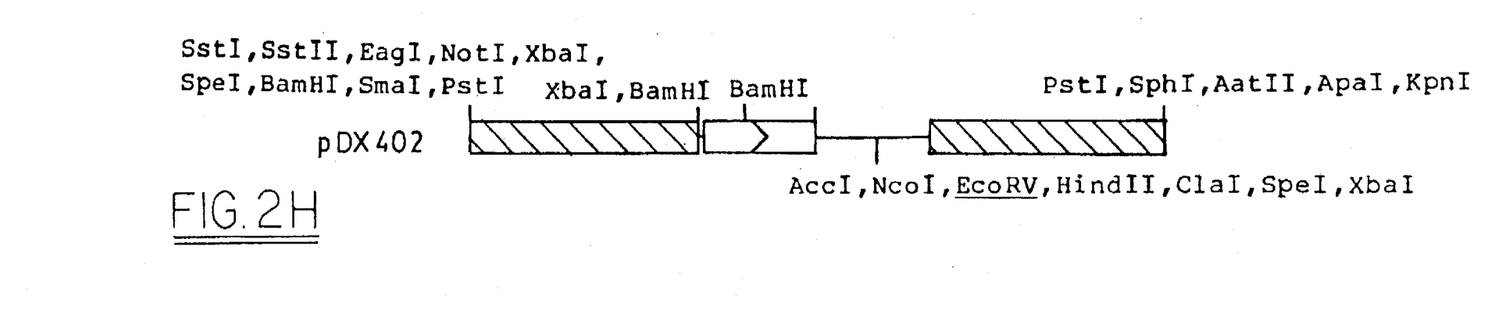
Figure 2I:
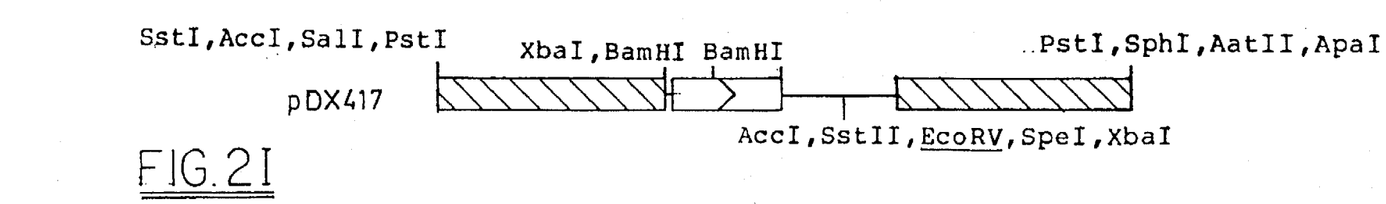
Figure 2J:
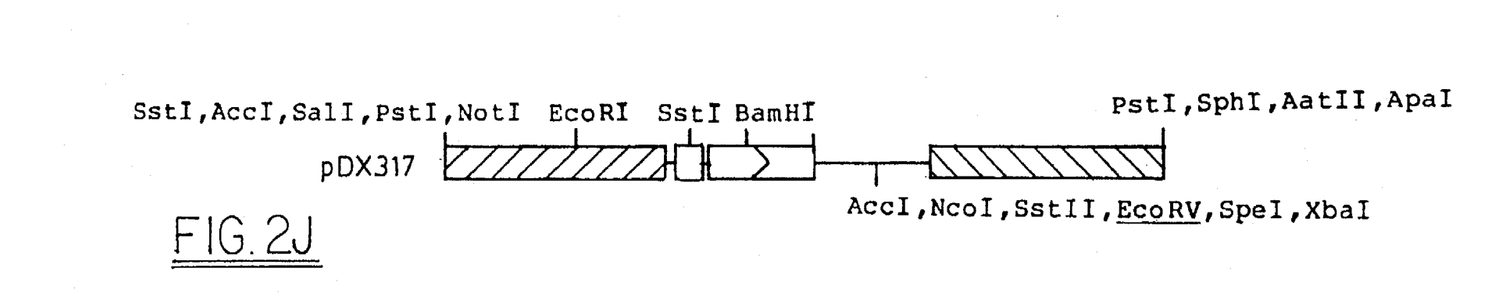

In simplest terms, the broad prime aspect of the present invention is to describe the use of a modified PinII promoter system based upon the wound inducible expression of a foreign gene of interest in monocot plants. These and other aspects of the present invention will become clearer in reference to the following description and appended figures in which FIG. 1 is a depiction of various genetic constructs made in accordance with the present invention; and FIG. 2 is a depiction of various expression vectors according to the present invention.

The initial step in making the present invention was to determine whether the PinII promoter from a dicot plant could be incorporated into a monocot plant, and if so, whether the promoter would function and respond to wounding. As described in our earlier U.S. patent application Ser. No. 07/762,680, filed Sep. 18, 1991, the disclosure of which is incorporated in toto herein, the 5' intron of the rice actin 1 gene (Act1), when inserted between the cauliflower mosaic virus CaMV 35S gene promoter and the β-glucuronidase (GUS) reporter gene greatly stimulated GUS activity in transformed rice protoplasts. A construct of the Act1 intron inserted between the PinII promoter and Gus reporter (which is replaced by a foreign gene of interest in accordance with the ultimate uses of the present invention) gene was constructed to determine if GUS activity would be stimulated.

Initially, the following two chimeric plasmids were constructed and used for transformation:

PinII promoter—GUS reporter

PinII promoter—Act1 intron—GUS reporter.

More specifically, the 5' intron from the rice Act1 gene was used to increase foreign gene expression from the promoter of the potato wound inducible protease inhibitor II gene (PinII) in transgenic rice. The 5' intron of the rice Act1 gene was found to significantly enhance the activity of the potato PinII promoter in transient assays of transformed protoplasts as shown in the following table:

| Construct Specific Names (nmol/hr/mg) | Structure | Mean GUS Activity |
|---|---|---|
| pDX106 | PinII promoter-GUS coding region-Nos 3' | 0.5 |
| pDX107 | PinII promoter-Act1 5' intron-GUS coding region-Nos 3' | 210.0 |
| pDX108 | PinII promoter-GUS coding region-PinII 3' | 0.5 |
| pDX109 | PinII promoter-Act1 5' intron-GUS coding region-PinII 3' | 121.0 |
| pAct1-D | Act1 promoter-GUS coding region-Nos 3' | 213.8 |

In the above table and throughout this description, Nos 3' refers to nopaline synthase gene 3' noncoding regions. In stable transformation experiments, rice protoplasts (4–10× $10^6$) were co-transformed with a PinII-based fusion plasmid (80 μg) and a selectable Act1-bar (glufosinate-ammonium resistant gene) construct (20 μg) using techniques described in U.S. patent application Ser. No. 07/762,680 and those well known in the art [see Theor. App. Genet. 76:835 (1988)]. Resistant calli were selected on 4 mg/l glufosinate ammonium using well known techniques. Each individual transformation produced between 400 and 600 resistant calli. Plantlet regeneration efficiency from resistant calli was between 10% and 20%, and the mean co-expression frequency was approximately 65% for Act1 5' intron-containing PinII-based fusion constructs.

The results from further analysis in transgenic rice plants, using those plasmids described in the above table and shown in FIG. 1, indicated that transgenic rice plants harboring the PinII-Gus construct produced low levels of GUS activity. However, the GUS activity was increased at least fifty-fold by the modified construct containing the Act1 intron. More importantly, GUS activity was greatly stimulated by mechanical wounding of the shoots of transgenic plants. The wound inducible effect is systemic because gentle wounding of a rice shoot in two small regions resulted in high level of GUS activity in the entire shoot. This finding is significant since, to our knowledge, there is no wound-inducible promoter that is known to function in rice or other cereal crops within the monocot subclass.

The wound inducible expression of natural insecticides at high levels in monocot plants using this modified PinII promoter system should provide adequate protection against insect attack. At the same time, as the insecticide is not expressed until such time as the plant is wounded or attacked by insects, and as the life of these insecticides in the plant is relatively short—measured in hours—the use of the promoter system should reduce the selection pressure on the development of resistant insects.

In order to localize the GUS activity driven by the PinII promoter, the tissue specific expression of the various PinII-Gus and PinII-Act1 5' intron-GUS constructs in wounded and non-wounded transgenic rice plants were assayed histochemically using the GUS substrate, 5-bromo-4-chloro-3-indolyl-β-D-glucuronic acid (X-Gluc); tissues showing blue coloration are indicative of GUS activity. In rice the PinII-GUS fusion construct showed relatively weak response to mechanical wounding. However, inclusion of the Act1 5' intron in the PinII-GUS fusion construct resulted in a high level wound-inducible response in stably transformed rice plants. The response was systemic and was not transmitted to tillers that were not connected to the wounded shoot by a common vascular system.

In order to make the wound-inducible promoter system according to the present invention more easily used for different applications, a number of PinII-based vectors were developed using techniques which have become well known and conventional in the art. The structure of the various PinII-based expression vectors are shown in FIG. 2.

The strategy for the construction of these vectors was (1) to isolate the PinII 3' end as a 1 kbp XbaI-SphI restriction fragment from pDXP3, and to clone this into the plasmid pCOR116 [see Mol. Gen. Genet. 231:150 (1991)] to produce the vector pDX316; (2) to isolate the PinII promoter-Act1 5' intron-Act1/GUS translational fusion junction region from plasmid pDX107 as a 1 kbp PstI-SmaI restriction fragment and clone this into the plasmid pBluescriptII-KS (Stratagene) to produce PinII-based expression vector pDX227 (this is translational fusion vectors containing the translation initiation codon from the Act1 gene followed by a polylinker region); (3) to remove the Act1 5' intron and Act1/GUS-translational fusion junction region from plasmids pDX107 and pDX 109 as a 0.9 kbp XbaI-SnaBI restriction fragment and replace these fragments with the Act1 5' intron and Act1/GUS translation fusion junction region from plasmid pBCG-A4 (containing an optimized translation initiation region and NcoI site at the Act1/GUS start codon) to produce plasmids pDX117 (from pDX107) and pDX119 (from pDX 109); (4) to remove the PinII promoter-Act1 5' intron-Act1 optimized start codon region from pDX117 and a 1.5 kbp PstI-NcoI restriction fragment and use this to replace the Act1 5' region of the Act1-based expression vectors pCOR102 and pCOR116 to produce the plasmids pDX202 (from pCOR102) and pDX216 (from pDX116); (5) to remove the PinII promoter and Act1 5' intron from pDX216 and a 1.5 kbp AccI restriction fragment and use this to replace the Act1 5' region of the Act1-based expression vector pCOR117 to produce the plasmid pDX217; (6) to isolate the PinII promoter and Act1 5' intron as a 1.5 kbp SalI-SpeI restriction fragment and use this to replace the Act1 5' region of pDX316 to produce the plasmid pDX427; (7) to isolate the 1 kbp PinII 3' end from pDX316 and add this to pDX202 as an EcoRV-ApaI restriction fragment to produce translational fusion vector pDX402, or to add this to pDX216 as a NcoI-SphI restriction fragment to produce translational fusion vector pDX416, or to add this to pDX217 as a SpeI-SphI restriction fragment to produce transcriptional fusion vector pDX417.

Plasmids pDX227, pDX202, pDX216, and pDX217 each contain the PinII promoter and Act1 5' intron followed by a polylinker sequence into which the foreign gene of interest (with its own 3' transcription terminator region) may be cloned. Plasmids pDX427, pDX402, pDX416 and pDX417 each contain a PinII 3' transcription terminator region following their PinII promoter and Act1 5' intron with a polylinker between the intron and 3'-end regions into which the coding region of the foreign gene of interest may be cloned. Different expression vectors according to the present invention, each containing several different restriction sites facilitate the cloning of useful foreign genes and subsequent manipulation of the resulting recombinant DNA molecules.

Each plasmid pDX227/pDX427, pDX202/pDX402, and pDX216/pDX416 according to the present invention contains an Act1 translation initiation codon in their polylinker region. These plasmids can be used for the creation of translation fusion constructs. Modification of the translation initiation codon region of the foreign genes of interest to create a NcoI restriction site facilitates the creation of fusion constructs using the pDX202/pDX402 and pDX216/pDX416 plasmids. In addition to having a wide variety of cloning sites in their respective polylinker regions, each of the translation fusion vectors according to the present invention contains a unique blunt-ended restriction site into which any suitably prepared foreign gene of interest may be cloned. As will become apparent to those skilled in the art examining the lower part of FIG. 2, blunt ended restriction sites (EcoRV or SmaI) are found in all three possible reading frames permitting the creation of translational fusion constructs with any suitably treated foreign gene of interest.

As will also become apparent to those skilled in the art, the transcriptional fusion vectors pDX217/pDX417 according to the present invention can be used to clone foreign genes that cannot tolerate N-terminal amino acid additions. Each vector contains no translation initiation codon. In addition to a choice of restriction sites in their respective polylinker region, they may each contain a unique blunt-ended restriction site (EcoRV, underlined) for the cloning of any suitable foreign gene of interest.

In addition, as will become apparent to those skilled in the art, viral translational enhancers, such as the alfalfa mosaic virus (AMV) enhancer [see Nature 325:622 (1987)], may also be included in the PinII expression vectors according to the present invention.

Specific chimeric plasmids according to the present invention may be constructed along a number of lines. For example, in making the PinII-Act1 5' intron-PinII gene construct according to the present invention, the constructs include:

PinII promoter-Act1 5' intron-PinII gene-PinII 3' region; and PinII promoter-Act1 5' intron-PinII gene-Nos 3' region.

Similarly, CPTi gene (Agricultural Genetics Company) containing constructs were made as above with the exception that the CPTi gene was substituted for the PinII gene.

In addition, as is apparent to those skilled in the art, it is possible to provide PinII-Act1 5' intron-PinII gene constructs according to the present invention containing an anti-viral DNA. Thus, the wound inducible promoter system according to the present invention can be expanded to include the control of insect-transmitted viral diseases. For example, the tungro virus infection of rice plants requires the participation of an insect vector. As the constructs according to the present invention may easily be modified by adding foreign DNA to the construct, such as by adding the anti-tungro viral DNA to a basic construct according to the present invention (PinII-Act1 5' intron-PinII gene-Nos 3' region), and rice can be transformed with this construct, the regenerated transgenic plants will synthesize very little PINII protein and anti-viral DNA. However, after insects bite the plants, large amounts of the PINII protein are produced to deter further insect attack, and the anti-viral DNA is produced to inhibit virus replication or production.

Although a number of protocols exist for transforming plants with the plasmid vectors according to the present invention, two such techniques which have been successful are the transformation of protoplasts using polyethylene glycol, and the transformation of suspended cell cultures using the DNA particle gun. Act1-bar constructs may also be used for co-transformation and for selecting regenerated calli that are resistant to 4–8 mg/liter of glufosinate ammonia.

In addition to the wound inducible gene promoter (PinII promoter) described above, a number of other wound inducible genes have been cloned and characterized from dicot plants by other investigators. For example, the genomic clones corresponding to Win1 and Win2 have been cloned from potato [see EMBO 9:593 (1990); and Mol. Gen. Genet. 215:200 (1989)]. In view of our finding that the PinII-Act1 chimeric system works in monocots, it is to be reasonably expected that the promoters of other wound inducible genes, such as Win1 and Win2, will also work in monocots, and thus other promoters of wound inducible genes are to be considered within the scope of the present invention.

Thus, while we have illustrated and described the preferred embodiment of our invention, it is to be understood that this invention is capable of variation and modification and we therefore do not wish or intend ourselves to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

We claim:

1. A wound inducible promoter construct for use in monocotyledonous plants consisting essentially of, in 5' to 3' order, a potato proteinase inhibitor II gene promoter and a 5' intron of rice actin 1 gene promoter.

2. A nucleic acid construct comprising:

a wound inducible promoter construct consisting essentially of, in 5' to 3' order, a potato proteinase inhibitor II gene promoter and a 5' intron of rice actin 1 gene promoter; and a foreign gene of interest under regulatory control of said wound inducible promoter construct.

3. A monocotyledonous plant comprising:

a wound inducible promoter construct consisting essentially of, in 5' to 3' order, a potato proteinase inhibitor II gene promoter and a 5' intron of rice actin 1 gene promoter; and a foreign gene of interest under regulatory control of said wound inducible promoter construct.

4. A rice plant comprising:

a wound inducible promoter construct consisting essentially of, in 5' to 3' order, a potato proteinase inhibitor II gene promoter and a 5' intron of rice actin 1 gene promoter; and a foreign gene of interest under regulatory control of said wound inducible promoter construct.

* * * * *